(12) United States Patent
Fukumoto

(10) Patent No.: US 9,249,517 B2
(45) Date of Patent: Feb. 2, 2016

(54) PROCESS FOR PRODUCTION OF REDUCED GLUTATHIONE

(75) Inventor: Kazunari Fukumoto, Yamaguchi (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 1035 days.

(21) Appl. No.: 13/375,630

(22) PCT Filed: Jun. 2, 2010

(86) PCT No.: PCT/JP2010/059361
§ 371 (c)(1),
(2), (4) Date: Feb. 1, 2012

(87) PCT Pub. No.: WO2010/140625
PCT Pub. Date: Dec. 9, 2010

(65) Prior Publication Data
US 2012/0118756 A1    May 17, 2012

(30) Foreign Application Priority Data
Jun. 3, 2009   (JP) .................................. 2009-134115

(51) Int. Cl.
| C25B 3/00 | (2006.01) |
| B01D 15/00 | (2006.01) |
| B01D 9/00 | (2006.01) |
| C01B 15/013 | (2006.01) |
| C25B 3/04 | (2006.01) |
| C07K 5/02 | (2006.01) |

(52) U.S. Cl.
CPC ................. *C25B 3/04* (2013.01); *C07K 5/0215* (2013.01)

(58) Field of Classification Search
CPC ............. C25B 3/04; B01D 15/00; B01D 9/00
USPC .......... 205/431, 443, 444; 210/660; 23/295 R
See application file for complete search history.

(56) References Cited

U.S. PATENT DOCUMENTS 4,771,126 A    9/1988  Hirotsuka et al.

FOREIGN PATENT DOCUMENTS

| CA | 869067 A | 4/1971 |
| CN | 86100959 A | 8/1986 |
| JP | 52-131527 A | 11/1977 |
| JP | 52-131528 A | 11/1977 |
| JP | 52131528 A * | 11/1977 ............ C07C 103/52 |

(Continued)

OTHER PUBLICATIONS

Roncato, "Studi Polarografici Applicati Alla Biochimica. Nota II: Sulla Riduzione Della Cistina Mediante it Catodo a Goccia di Mercurio", Arch. Sci. Biol. (no month, 1934), vol. 20, pp. 146-171.*

(Continued)

*Primary Examiner* — Edna Wong
(74) *Attorney, Agent, or Firm* — Leydig, Voit & Mayer, Ltd.

(57) ABSTRACT

Provided is a superior method of producing reduced glutathione by electroreduction of oxidized glutathione. In a method of producing reduced glutathione by electroreduction of oxidized glutathione using a cathode cell and an anode cell separated from each other by a separating membrane, oxidized glutathione is produced using an aqueous oxidized glutathione solution with pH 2.0-3.0 comprising a conducting agent other than acid as a solution in the cathode cell.

11 Claims, 2 Drawing Sheets

(56) References Cited

FOREIGN PATENT DOCUMENTS

| JP | 59-009184 A | 1/1984 |
|----|-------------|--------|
| JP | 08-041671 A | 2/1996 |

OTHER PUBLICATIONS

Kolthoff et al., "The Reduction of Cystine at the Dropping Mercury Electrode", Journal of the American Chemical Society (Feb. 1941), vol. 63, No. 2, pp. 520-526.*
Dohan et al., *Journal of Biological Chemistry*, 129: 393-403 (1939), no month.
Jin et al., *Electroanalysis*, 12(11): 858-862 (2000), no month.
Stricks et al., *Journal of the American Chemical Society 74(18)*: 4646-4653 (1952), no month.
European Patent Office, Extended European Search Report in European Application No. 10783407.9 (Jan. 15, 2013).
Japanese Patent Office, International Search Report in International Patent Application No. PCT/JP2010/059361 (Jul. 27, 2010).
Japanese Patent Office, Written Opinion in International Patent Application No. PCT/JP2010/059361 (Jul. 27, 2010).
Biovision, Inc., "Oxidized Glutathione (GSSG)," CAS No. 27025-41-8, catalog # 1241-1 product description (retrieved at URL http://www.biovision.com/oxidized-glutathione-gssg-2994.html on Mar. 5, 2015).
Pan et al., "Purification of Reduced Glutathione (GSH) by Ion Exchange Resin," *Biotechnology*, 16(4): 38-41 (Aug. 2006).
Chinese Patent Office, Notification of The Second Office Action in Chinese Patent Application No. 201080034332.1 (Oct. 29, 2014).

* cited by examiner

PROCESS FOR PRODUCTION OF REDUCED GLUTATHIONE

TECHNICAL FIELD

The present invention relates to a method of producing reduced glutathione by electroreduction of oxidized glutathione.

BACKGROUND ART

As a method of electroreduction of a disulfide compound, a method using an alloy consisting of two or more kinds of particular metals as a cathode is known (patent document 1). In addition, as a method of producing L-cysteine by electroreduction of L-cystine, which is one kind of disulfide compound, a method using a cation exchange membrane as a separating membrane, and an L-cystine solution acidified by adding a mineral acid such as hydrochloric acid and the like to a cathode side electrolytic cell is known (patent document 2). As a method of producing reduced glutathione by electroreduction of oxidized glutathione, a method using an aqueous oxidized glutathione solution acidified by adding a mineral acid such as concentrated hydrochloric acid and the like to a cathode side electrolytic cell is also known (patent document 3).

However, the above-mentioned electroreduction methods of a disulfide compound require use of an expensive electrode. When oxidized glutathione is electroreduced under L-cystine electroreduction conditions described in patent document 2, reduced glutathione cannot be produced in a sufficient yield, since it is unstable under strong acidity and high temperature, as compared to L-cysteine. The method described in patent document 3 also uses, similar to the method described in patent document 2, aqueous oxidized glutathione solution strongly acidified to pH 0.6-1.0 by adding a mineral acid, and therefore, it is associated with the problems of corrosion of cathode and decomposition of reduced glutathione. To minimize the decomposition of reduced glutathione under strong acidity, it is necessary to lower the electric current density. In this case, however, reduction efficiency per electrode area decreases, and therefore, efficient production of reduced glutathione cannot be achieved unless the electrode area is increased instead. That is, production of reduced glutathione in an industrial scale by electroreduction of aqueous oxidized glutathione solution strongly acidified with a mineral acid requires huge electroreduction facility corresponding to the sizes of ion exchange membrane and electrode, as well as a special electrode capable of resisting corrosion. Therefore, a production method of reduced glutathione by conventional electroreduction is not entirely a realistic method in terms of production efficiency and facility.

DOCUMENT LIST

Patent Documents patent document 1: JP-A-H8-41671
patent document 2: JP-A-S59-9184
patent document 3: JP-A-S52-131528

SUMMARY OF THE INVENTION

Problems to be Solved by the Invention

In a method of producing reduced glutathione by electroreduction of oxidized glutathione, improvement of reduction efficiency is demanded to reduce the necessary areas of electrode and ion exchange membrane to realistic sizes, while suppressing the corrosion of cathode and decomposition of reduced glutathione.

Means of Solving the Problems

The present invention relates to the method described in the following (1)-(7).

(1) A process for producing reduced glutathione by electroreduction of oxidized glutathione using a cathode cell and an anode cell separated from each other by a separating membrane, wherein a solution in the cathode cell comprises an aqueous oxidized glutathione solution with pH 2.0-3.0 comprising a conducting agent other than acid.
(2) The process according to (1), wherein the conducting agent other than acid is a neutral salt.
(3) The process according to (2), wherein the neutral salt is sodium sulfate, sodium chloride, potassium sulfate or potassium chloride.
(4) The process according to any one of (1)-(3), wherein the conducting agent other than acid has a concentration of 0.05 mol/L or more and 5.0 mol/L or less.
(5) The process according to any one of (1)-(4), wherein the aqueous oxidized glutathione solution has a concentration of 50 g/L or more.
(6) The process according to any one of (1)-(5), wherein the electroreduction is carried out at an electric current density of 0.1-30 A/dm$^2$.
(7) A process for producing a reduced glutathione crystal which comprises passing reduced glutathione produced by the process according to any one of (1)-(6) through an ion exchange column to obtain a desalted aqueous reduced glutathione solution, and thereafter crystallizing reduced glutathione.

Effect of the Invention

The present invention can produce reduced glutathione efficiently in an industrial scale.

DESCRIPTION OF EMBODIMENTS

Figure 1A:
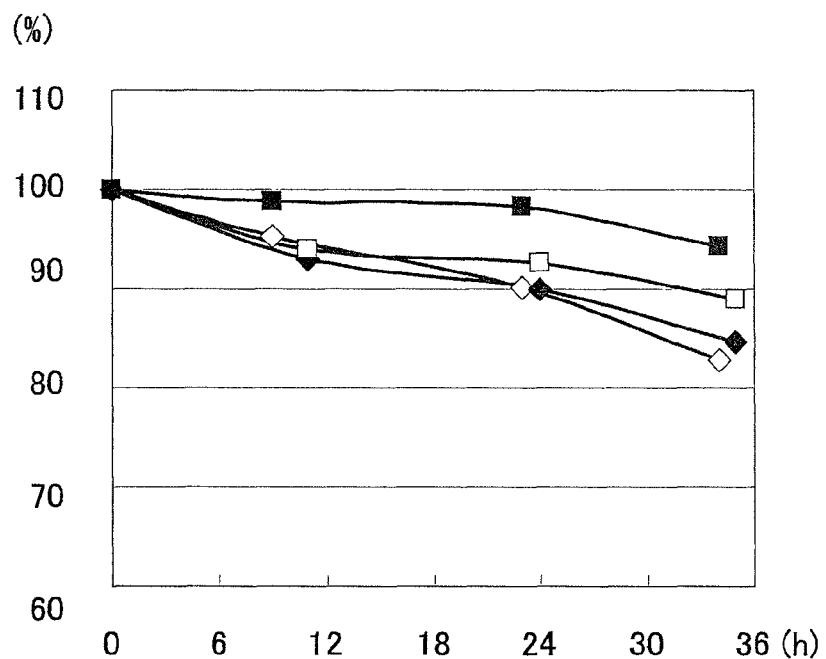
FIG. 1A is a drawing showing the time-course changes of the residual ratio of reduced glutathione at each pH.

The method of the present invention is, in a method of producing reduced glutathione by electroreduction of oxidized glutathione using a cathode cell and an anode cell separated from each other by a separating membrane, a method comprising using an aqueous oxidized glutathione solution with pH 2.0-3.0 comprising a conducting agent other than acid as a cathode cell solution.

The conducting agent other than acid is a substance other than acid, which has an action of decreasing the pH of an aqueous oxidized glutathione solution when added to the aqueous solution, such as inorganic acids such as hydrochloric acid, sulfuric acid and the like, and organic acids such as acetic acid, propionic acid and the like, and is not particularly limited as long as it is a conducting agent that enhances the electrical conductivity of the aqueous solution. As such conducting agent, a neutral salt can be preferably mentioned. Examples of the neutral salt include inorganic salts such as sulfate, nitrate, chlorine salt, phosphate and the like, organic salts such as acetate, propionate and the like, and the like. Examples of the salt constituting the neutral salt include metal salts such as sodium, potassium, magnesium and the like, ammonium salt and the like. Particularly preferable examples of the conducting agent include sodium sulfate, sodium chloride, potassium sulfate and potassium chloride, and the most preferred is sodium sulfate.

The aqueous oxidized glutathione solution containing a neutral salt may be prepared by directly dissolving a neutral salt in said solution, or may be prepared by mixing an acid with an alkali to form a neutralized salt in said aqueous solution.

The pH of the aqueous oxidized glutathione solution is preferably pH 2.0-3.0, more preferably pH 2.5-2.9, particularly preferably pH 2.8-2.9, since reduced glutathione produced by electroreduction decomposes under strong acidity, and electroreduction does not proceed near neutrality.

The concentration of the conducting agent is not particularly limited as long as it is not more than the saturation concentration in an aqueous oxidized glutathione solution. For example, when sodium sulfate is used as a conducting agent, the concentration is 0.05-5.0 mol/L, preferably 0.2-3.0 mol/L, more preferably 0.4-1.0 mol/L.

The method of the present invention can enhance electrical conductivity of an aqueous oxidized glutathione solution without decreasing the pH of the aqueous oxidized glutathione solution, by adding a conducting agent other than acid to said solution. Hence, the impedance of the solution is low as compared to that of an aqueous oxidized glutathione solution without a conducting agent when the same electric current is electrified, and therefore, the temperature of the aqueous solution does not become high. That is, the decomposition of reduced glutathione in a cathode cell can be suppressed.

As mentioned above, by electroreduction of an aqueous oxidized glutathione solution containing a conducting agent other than acid in a cathode cell, the production efficiency of reduced glutathione can be increased while suppressing the decomposition thereof. As a result, the separating membrane and electrode can be downsized, and the facility cost can be kept low.

The production method of the present invention is also characterized by the use of a supersaturated aqueous oxidized glutathione solution as an aqueous oxidized glutathione solution for a cathode cell.

The saturation solubility of oxidized glutathione in water at ambient temperature (25° C.) is 20 g/L or less, and the solubility does not increase even in the co-presence of a salt, as long as the pH is not greatly changed. However, it has been found that oxidized glutathione, once dissolved, has extremely high supersaturation solubility over 300 g/L. This supersaturation state is stable at ambient temperature, and requires several days before crystallizing. Utilizing this characteristic, a solution of oxidized glutathione with concentration beyond saturation solubility can be prepared. As mentioned above, moreover, since addition of a conducting agent other than acid imparts superior electrical conductivity to a supersaturated aqueous oxidized glutathione solution, more efficient electroreduction of oxidized glutathione is possible. While the concentration of the supersaturated aqueous oxidized glutathione solution containing a conducting agent other than acid is not limited as long as it can maintain supersaturation state, it is 50 g/L or more, preferably 100 g/L or more, more preferably 150 g/L or more, further preferably 200 g/L or more, most preferably 300 g/L or more.

In addition, utilizing the above-mentioned supersaturation, even when an aqueous oxidized glutathione solution having strong acidity of pH 0.6-1.0 by adding acid is used as a cathode cell solution, as long as the solution is a supersaturated aqueous oxidized glutathione solution of 200 g/L or more, the reduction rate is far higher than the decomposition rate of reduced glutathione under strong acidity. Thus, using, as a cathode, an electrode made of an economical material that is not easily corroded even under strong acidity, reduced glutathione can be produced efficiently and economically.

The preparation method of a supersaturated solution of oxidized glutathione is not limited, and a method including dissolving oxidized glutathione in an alkali solution at a high concentration and desalting, a method including adsorbing oxidized glutathione to an ion exchange resin and eluting it in a solution having a high concentration, a method including concentrating a solution with a concentration not more than saturation solubility, and the like can be mentioned.

The solution for an anode cell in the present invention is not particularly limited as long as it is a conductive aqueous solution, and inorganic acid solutions of hydrochloric acid, sulfuric acid and the like, organic acid solutions of acetic acid, propionic acid and the like, a solution dissolving a conducting agent other than acid and the like can be mentioned. As for the concentration of inorganic acid and organic acid, conductivity is low at low concentrations, and ion exchange membrane is easily deteriorated at high concentrations. Therefore, the concentration thereof to be used is 0.5-3 mol/L, preferably 1-2 mol/L. Examples of the conducting agent other than acid include one contained in the aqueous oxidized glutathione solution in the above-mentioned cathode cell, with preference given to the same conducting agent as the one contained in an aqueous oxidized glutathione solution.

The concentration of the conducting agent in the solution in an anode cell is preferably of the same level as that of the conducting agent in the solution in a cathode cell. For example, when sodium sulfate is used as a conducting agent, the concentration is 0.05-5.0 mol/L, preferably 0.2-3.0 mol/L, more preferably 0.4-1.0 mol/L.

As the cathode to be used in the method of the present invention, a metal having a hydrogen overvoltage of not less than that of carbon is preferably used. Examples of such metal include zinc, lead and carbon, and porous carbon, and more preferred is zinc.

As the anode to be used in the method of the present invention, any metal can be used as long as it is an insoluble metal. A metal superior in the corrosion resistance is preferable and, for example, titanium plated with platinum, platinum-iridium, lead, lead alloy, lead dioxide and titanium oxide can be mentioned. Preferred is titanium plated with platinum.

As the separating membrane to be used in the method of the present invention, any membrane can be used as long as it can reduce leakage of reduced glutathione produced in the cathode cell into the anode cell. Preferred is an ion exchange membrane, more preferred is a cation exchange membrane, specifically SELEMION CMT (manufactured by Asahi Glass Company).

In the method of the present invention, electric current density, voltage, temperature and the like are not particularly limited. As conditions for improving reduction efficiency while suppressing decomposition of the produced reduced glutathione, the electric current density is preferably 0.1-30 $A/dm^2$, more preferably 0.5-20 $A/dm^2$, further preferably 1-10 $A/dm^2$, the voltage is preferably 1-20 V, more preferably 2-15 V, further preferably 3-10 V, and the temperature is preferably 4-50° C., more preferably 10-30° C., further preferably 10-25° C.

After completion of electroreduction, a solution in the cathode cell which contains the produced reduced glutathione is desalted by passing through an ion exchange column, and the aqueous desalted reduced glutathione solution can be directly used for crystallization. Examples of the ion exchange resin include strongly acidic cation exchange resins represented by SK-116 and SK-104 (both DIAIONs, manufactured by Mitsubishi Chemical Corporation), and weakly basic ion exchange resins represented by WA-30 and WA-21 (both DIAIONs, manufactured by Mitsubishi Chemical Corporation). The desalted reduced glutathione can be crystallized by concentration, appropriate addition of a solvent or seed crystal, and cooling.

Example 1 pH Stability of Reduced Glutathione

Figure 1B:
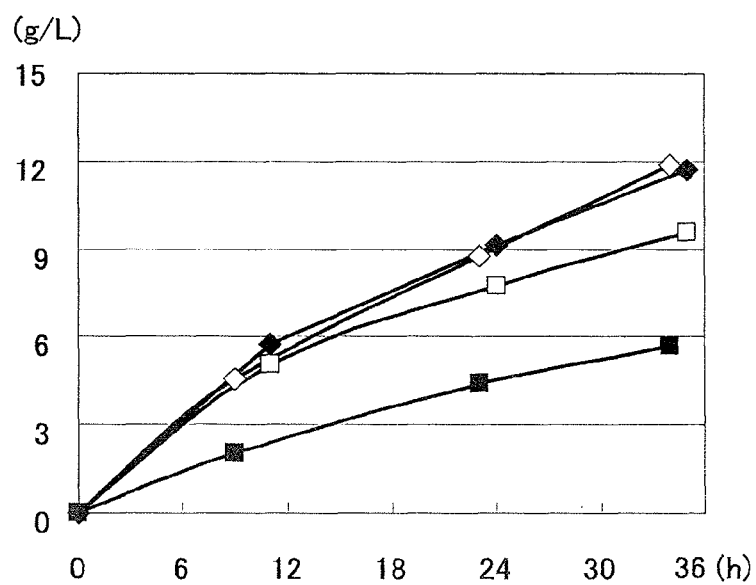
FIG. 1B is a drawing showing the time-course changes of the increased amount of impurity in an aqueous reduced glutathione solution at each pH. The vertical axis of FIG. 1A shows the residual ratio of reduced glutathione, and the horizontal axis shows the elapsed time (hours). The vertical axis of FIG. 1B shows the content (g/L) of impurity in the aqueous reduced glutathione solution, and the horizontal axis shows the elapsed time (hours).

Using an aqueous reduced glutathione solution (100 g/L, pH 2.90) and sulfuric acid, aqueous reduced glutathione solutions (100 g/L) adjusted to pH 0.6, 1.2 and 2.0 were produced. Each solution was preserved at 25° C. for 24-36 hr, and the residual amount of reduced glutathione was quantified by high performance liquid chromatography (HPLC) under the following conditions. As shown in FIG. 1A, a solution at pH 2.0 or less was found to have a lower reduced glutathione residual ratio as compared to a solution at pH 2.90. Furthermore, as shown in FIG. 1B, a solution at pH 2.0 or less was found to show a higher increased amount of impurity due to hydrolysis as compared to a solution at pH 2.90. As for the impurity, the total amount of the substances other than reduced glutathione and oxidized glutathione was quantified under the following HPLC conditions, and the concentration (g/L) converted to reduced glutathione was calculated.

HPLC Conditions
column: Nucleosil 100-5 C18 φ4.6×150 mm
column temperature: 40° C.
buffer: 10% acetonitrile solution containing 0.405% sodium 1-heptanesulfonate (adjusted to pH 2.0 with phosphoric acid)
flow rate: 1.0 mL/min
detector: UV detector (wavelength 210 nm)

Example 2

Electroreduction of Oxidized Glutathione Using Sodium Sulfate as Conducting Agent An aqueous oxidized glutathione solution (about 400 g/L) was prepared by adding sodium hydroxide to adjust pH to 7.0, and passed through a cation exchange resin for desalting to prepare a supersaturated aqueous oxidized glutathione solution (about 350 g/L). The solution was diluted and sodium sulfate was added to prepare an aqueous oxidized glutathione solution (310 g/L) containing 0.75 mol/L sodium sulfate. The pH of the solution was 2.91.

The electrolytic cell used contained anode side (150 mL) and cathode side (300 mL), and the both were separated by a 50 $cm^2$ cation exchange membrane SELEMION CMT (manufactured by Asahi Glass Company). As the anode, a 50 $cm^2$ platinum-plated titanium plate was used and, as the cathode, a 50 $cm^2$ zinc plate was used. The anode cell contained 0.50 mol/L sulfuric acid solution (140 mL), and the cathode cell contained the aqueous oxidized glutathione solution (280 mL) prepared above.

An electroreduction reaction was performed at electrolytic voltage 5-6V, electrolytic electric current 3.0 Å, at room temperature for 10 hr. The resultant product in the cathode cell was quantified by HPLC under the same conditions as in Example 1 and 79.7 g of reduced glutathione was confirmed to have been produced (conversion ratio 91.8%).

Under the above-mentioned electroreduction conditions, corrosion of cathode was hardly seen. However, when 150 g/L aqueous oxidized glutathione solution adjusted to pH 0.68 with sulfuric acid was used as the cathode cell solution under the above-mentioned electroreduction conditions, instead of the aqueous oxidized glutathione solution containing 0.75 mol/L sodium sulfate, elution of zinc used for cathode in the cathode cell solution was observed.

Example 3

Electroreduction Rate Using Supersaturated Aqueous Oxidized Glutathione Solution About 350 g/L supersaturated aqueous oxidized glutathione solution prepared in Example 2 was diluted to prepare 300 g/L, 200 g/L, 150 g/L and 100 g/L aqueous oxidized glutathione solutions, each containing 0.75 mol/L sodium sulfate. The respective solutions had pH 2.89.

The electrolytic cell, cation exchange membrane and cathode and anode used were the same as those in Example 2. The anode cell contained 0.50 mol/L sulfuric acid solution (140 mL), and the cathode cell contained the aqueous oxidized glutathione solution (280 mL) prepared above.

Figure 2:
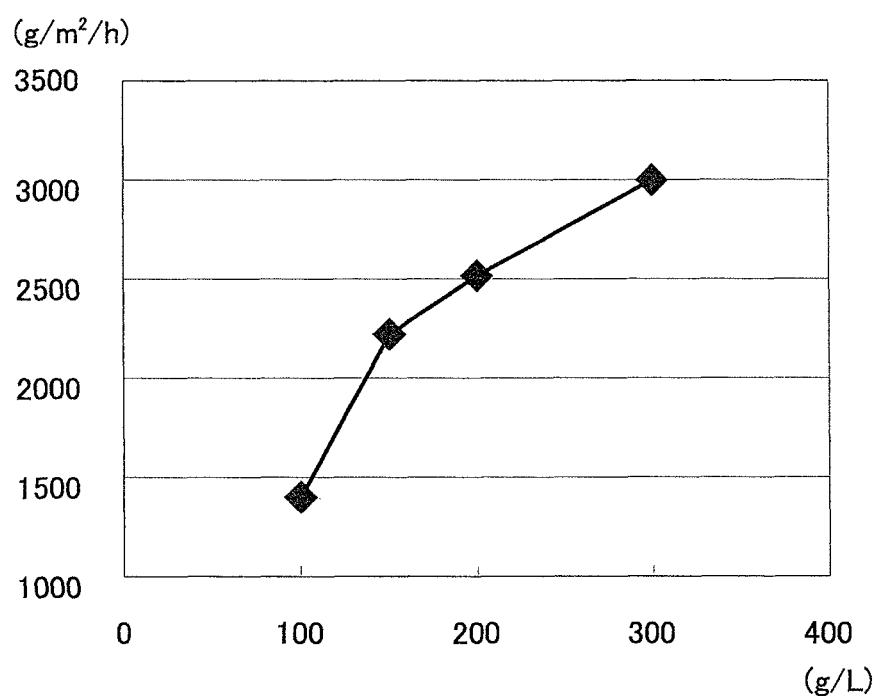
FIG. 2 is a drawing showing the relationship between the concentration of oxidized glutathione in a cathode cell solution and the electroreduction rate. The vertical axis shows the electroreduction rate (g/m$^2$/h), and the horizontal axis shows the oxidized glutathione concentration (g/L).

An electroreduction reaction was performed at electrolytic voltage 5-7V, electrolytic electric current 3.0 Å and at room temperature. The resultant product in the cathode cell was quantified by HPLC under the same conditions as in Example 1. It has been found that a higher concentration of an aqueous oxidized glutathione solution placed in the cathode cell shows a higher electroreduction rate, and particularly, high electroreduction rate is obtained at 150 g/L or more (FIG. 2).

Example 4

Production of Reduced Glutathione Crystals

The aqueous reduced glutathione solution obtained in Example 2 was passed through a strongly acidic cation exchange resin SK-116(H+) (manufactured by Mitsubishi Chemical Corporation), and then weakly basic anion exchange resin WA-21(OH−) (manufactured by Mitsubishi Chemical Corporation) to remove coexisting salts. The obtained reduced glutathione-containing fraction was concentrated under reduced pressure, and a seed crystal was added to cause crystallization to obtain reduced glutathione as crystals.

INDUSTRIAL APPLICABILITY

The method of the present invention has enabled an industrial scale production of reduced glutathione by electroreduction of oxidized glutathione.

EXPLANATION OF SYMBOLS

In FIG. 1, ◇ shows aqueous reduced glutathione solution at pH 0.6, ♦ at pH 1.2, ☐ at pH 2.0, and ■ at pH 2.9.

The invention claimed is:

1. A process for producing reduced glutathione comprising:
   (a) providing a cathode cell and an anode cell separated from each other by a separating membrane, wherein the cathode cell comprises an aqueous oxidized glutathione solution with pH 2.0-3.0, wherein the aqueous oxidized glutathione solution comprises a conducting agent other than acid, and wherein the oxidized glutathione is present in the aqueous oxidized glutathione solution at a concentration of 200 g/L or more, and
   (b) electroreducing the oxidized glutathione to produce reduced glutathione.

2. The process according to claim 1, wherein the conducting agent other than acid is a neutral salt.

3. The process according to claim 2, wherein the neutral salt is sodium sulfate, sodium chloride, potassium sulfate or potassium chloride.

4. The process according to claim 3, wherein the conducting agent other than acid is present in the aqueous oxidized glutathione solution at a concentration of 0.05-5.0 mol/L.

5. The process according to claim 4, wherein the electroreduction is carried out at an electric current density of 0.1-30 A/dm$^2$.

6. The process according to claim 2, wherein the conducting agent other than acid is present in the aqueous oxidized glutathione solution at a concentration of 0.05-5.0 mol/L.

7. The process according to claim 6, wherein the electroreduction is carried out at an electric current density of 0.1-30 A/dm$^2$.

8. The process according to claim 1, wherein the conducting agent other than acid is present in the aqueous oxidized glutathione solution at a concentration of 0.05-5.0 mol/L.

9. The process according to claim 1, wherein the electroreduction is carried out at an electric current density of 0.1-30 A/dm$^2$.

10. The process of claim 1, wherein the aqueous oxidized glutathione solution is prepared by (i) dissolving oxidized glutathione in water at pH 7.0, and (ii) adjusting the pH to pH 2.0-3.0.

11. A process for producing a reduced glutathione crystal which comprises:
    (a) providing a cathode cell and an anode cell separated from each other by a separating membrane, wherein the cathode cell comprises an aqueous oxidized glutathione solution with pH 2.0-3.0, wherein the aqueous oxidized glutathione solution comprises a conducting agent other than acid, and wherein the oxidized glutathione is present in the aqueous oxidized glutathione solution at a concentration of 200 g/L or more,
    (b) electroreducing the oxidized glutathione in the aqueous oxidized glutathione solution to produce an aqueous reduced glutathione solution,
    (c) passing the aqueous reduced glutathione solution through an ion exchange column to obtain a desalted aqueous reduced glutathione solution, and
    (d) thereafter crystallizing reduced glutathione from the desalted aqueous reduced glutathione solution.

* * * * *